United States Patent [19]

Ahmed

[11] Patent Number: 5,968,969
[45] Date of Patent: Oct. 19, 1999

[54] STABLE, LONG ACTING SALTS OF CARBOXAMIDES FOR THE TREATMENT OF JOINT DISEASE

[75] Inventor: Imran Ahmed, East Lyme, Conn.

[73] Assignee: Pfizer Inc, New York, N.Y.

[21] Appl. No.: 08/914,728

[22] Filed: Aug. 19, 1997

Related U.S. Application Data

[60] Provisional application No. 60/024,247, Aug. 21, 1996.
[51] Int. Cl.⁶ .......................... A01N 43/38; C07D 209/34
[52] U.S. Cl. ............................................. 514/414; 548/468
[58] Field of Search .............................. 548/468; 514/414

[56] References Cited

U.S. PATENT DOCUMENTS 4,556,672  12/1985  Kadin ....................................... 514/414
5,036,099  7/1991  Allen et al. ............................. 514/414

FOREIGN PATENT DOCUMENTS 337628  10/1989  European Pat. Off. .
498588   8/1992  European Pat. Off. .
9416694  8/1994  WIPO .

OTHER PUBLICATIONS

Berge, et al., Pharmaceutical Salts, *J. Pharm Sci.,* 66(1), pp. 1–19 (1977).

*Primary Examiner*—Robert W. Ramsuer
*Assistant Examiner*—Dominic Keating
*Attorney, Agent, or Firm*—Peter C. Richardson; Paul H. Ginsburg; Raymond M. Speer

[57] ABSTRACT

Calcium, magnesium, lidocaine and benzathine salts of 2-oxindole-1-carboxamides are useful for the treatment of joint disease by intra-articular administration.

6 Claims, No Drawings

STABLE, LONG ACTING SALTS OF CARBOXAMIDES FOR THE TREATMENT OF JOINT DISEASE

This application claims the priority benefit of U.S. Provisional Application No. 60/024,247 filed Aug. 21, 1996.

This invention provides stable, long acting salts of anti-inflammatory carboxamides, especially salts of (z)-5-chloro-2,3-dihydro-3-(hydroxy-2-thienylmethylene)-2-oxo-1-H-indole-1-carboxamide (tenidap) which are useful as analgesic or anti-inflammatory agents in the treatment of joint disease.

BACKGROUND OF THE INVENTION

Kadin, U.S. Pat. No. 4,556,672 disclosed 2-oxindole-1-carboxamides of the formula

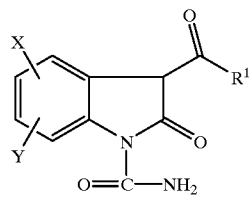

and pharmaceutical salts thereof which include tenidap and its salts.

Allen and O'Neill, U.S. Pat. No. 5,036,099 disclosed an anhydrous crystalline form of the sodium salt of tenidap which is nonhygroscopic and stable in dosage forms.

Tenidap and other 2-oxindole-1-carboxamides are acute phase protein modulating anti-inflammatory drugs which are useful for the treatment of rheumatoid arthritis. Similar to the steroids, these compounds have been shown to cause rapid reduction in acute phase proteins in arthritic patients. Intra-articular administration of these compounds relieves joint pain and swelling while minimizing systemic drug exposure. Prolonged-acting formulations employing sparingly soluble salts are required for intra-articular administration.

SUMMARY OF THE INVENTION

This invention provides the magnesium, calcium, lidocaine and benzathine salts of 2-oxindole-1-carboxamides of the formula

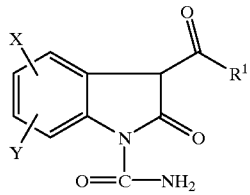

I wherein X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

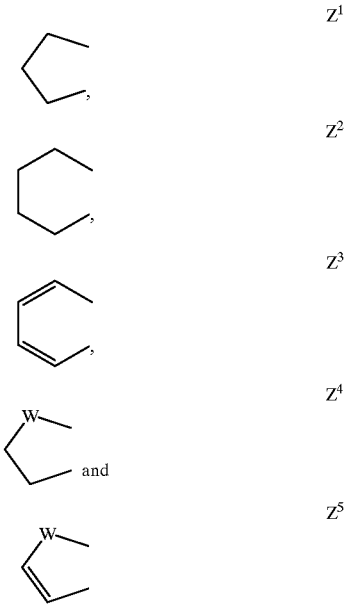

wherein W is oxygen or sulfur;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)-alkyl having 1 to 3 carbons in said alkyl, naphthyl, bicyclo[2.2.1]heptan-2-yl, bicyclo[2.2.1]hept-5-en-2-yl and $-(CH_2)_n-Q-R^O$;

wherein the substituent on said substituted phenyl, said (substituted phenyl)alkyl and said (substituted phenoxy) alkyl is selected from the group consisting of fluoro, chloro, bromo, alkyl having 1 to 4 carbons, alkoxy having 1 to 4 carbons and trifluoromethyl, n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b] thiophene; and $R^O$ is hydrogen or alkyl having 1 to 3 carbons.

These salts are sparingly soluble in water and are suitable for intra-articular injection to alleviate pain and swelling associated with joint disease.

Especially preferred compounds are the calcium and benzathine salts of 5-chloro-2,3-dihydro-3-(hydroxy-2-thienyl-methylene)-2-oxo-1-H-indole-1-carboxamide and 5-fluoro-6-chloro-2,3-dihydro-3-(hydroxy-2-thienylmethylene)-2-oxo-1-H-indole-1-carboxamide.

The first referenced compound forming calcium and benzathine salts has the established name "tenidap" as authorized by the *USP Dictionary of USAN* and *International Drug Names* 1998, Nomenclature Committee of the USP Committee of Revision, U.S. Pharmacopeia, 12601 Twinbrook Parkway, Rockville, Md. 20852, and may be represented by the formula:

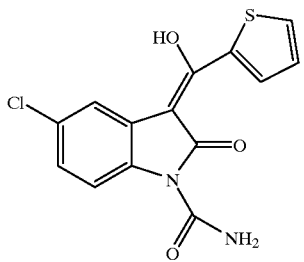

The second referenced compound forming calcium and benzathine salts has the established name "ilonidap" as authorized by said *USP Dictionary,* and may be represented by the formula:

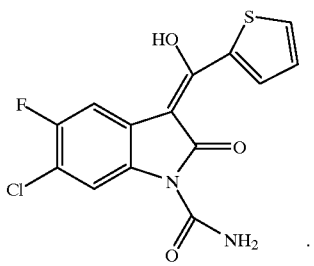

In another aspect, this invention provides a method for treating joint disease comprising intra-articular injection of a calcium, magnesium, lidocaine or benzathiene salt of a compound of formula I.

In another aspect, this invention provides a pharmaceutical composition suitable for intra-articular injection of the calcium, magnesium, lidocaine or benzathine salt of a compound of formula I and a pharmaceutically acceptable carrier.

In another aspect, this invention comprises a salt-selected from the group consisting of magnesium, calcium, benzothiene and lidocaine of a compound of the formula

II

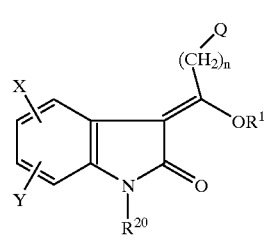

wherein X is H, F, Cl, Br, $(C_1-C_6)$alkyl, $(C_3-C_8)$cycloalkyl, $NO_2$, $CF_3$, CN, SH, $S(O)_mR^3$, $OR^4$, $COR^4$ or $CONR^4R^5$;

Y is H, F, Cl, Br, $(C_1-C_6)$alkyl, $(C_3-C_8)$cycloalkyl, $NO_2$, $CF_3$, CN, SH, $S(O)_tR^{17}$, $OR^{18}$, or $CONR^{18}R^{19}$;

$R^1$ is H;

$R^{20}$ is $COR^6$, $CONR^7R^8$, phenyl or mono- or disubstituted phenyl wherein the substituent or substituents are each Cl, F, Br, $(C_1-C_6)$alkyl, $(C_1-C_6)$alkoxy, or, $CF_3$;

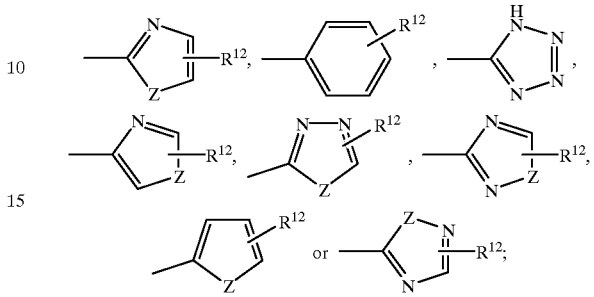

B is H, F, Cl, Br, I, $CF_3$, $OR^{13}$, $S(O)_pR^{14}$, $COOR^{15}$, $CONR^{13}R^{15}$, CN, $NO_2$, $COR^{14}$, $CH_2OR^{15}$, $OCOR^{14}$, $NR^{13}R^{15}$, $N(R^{13})COR^{15}$, or $SO_2NR^{13}R^{15}$, provided that A and B cannot both be H, or A and B are taken together, bonded to the same ring carbon of $Q^1$ and equal oxo, or when A is not H, B is as defined above or $(C_1-C_4)$alkyl;

$A^1$ is F, Cl, Br, I, $CF_3$, $OR^9$, $S(O)_pR^{10}$, $COOR^{11}$, $CONR^9R^{11}$, CN, $NO_2$, $COR^{10}$, $CH_2OR^{11}$, $OCOR^{10}$, $NR^9R^{11}$, $N(R^9)COR^{11}$, or $SO_2NR^9R^{11}$;

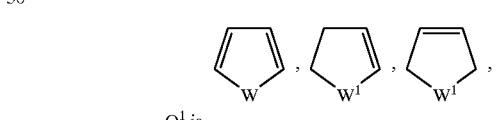

$Q^1$ is

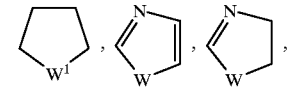

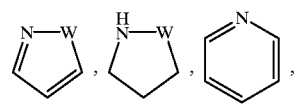

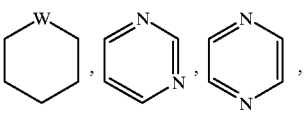

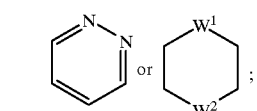

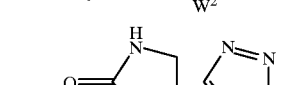

$Q^2$ is

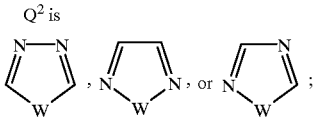

m, n, p, q and t are each zero, one or two;

W and Z are each O, S or $NR^{11}$;

$W^1$ and $W^2$ are each O, S or $NR^{10}$, provided that when one of $W^1$ and $W^2$ is O, S or the other is O or S;

$R^3$, $R^6$, $R^{10}$, $R^{14}$ and $R^{17}$ are each $(C_1-C_6)$alkyl or phenyl;

$R^5$, $R^8$, $R^{11}$, $R^{15}$ and $R^{19}$ are each H, $(C_1-C_6)$alkyl or phenyl;

$R^4$, $R^7$, $R^9$, $R^{13}$ and are each H or $(C_1-C_6)$alkyl; and $R^{12}$ is H, F, Cl, Br, $CF_3$ or $(C_1-C_6)$alkyl.

DETAILED DESCRIPTION OF THE INVENTION

Tenidap, an oxindole, is an acute phase protein modulating anti-inflammatory drug intended for use in the treatment of rheumatoid arthritis. Similar to the steroids, the oxindoles have been shown to cause rapid reduction in acute phase proteins in arthritic patients and in in vitro studies have been shown to inhibit production of IL-6 and IL-1. These properties suggested the use of tenidap and other oxindoles for intra-articular treatment for arthritis. B. H. Littman, et al. Arthritis and Rheumatism 35/9 Suppl., S341, 1992. An intra-articular suspension dosage form of tenidap free acid was developed as a two-vial product. One vial contained sterile tenidap free acid that was aseptically synthesized and aseptically jet milled. The second vial consisted of a sterile, aqueous, buffered constituting vehicle containing a surfactant. Upon constituting the drug substance with the vehicle the product needed to be vortexed to provide uniform dispersibility of the drug as well as to insure delivery of the required dose.

After an open clinical study, a placebo controlled, double-blind clinical study was conducted in patients with rheumatoid-arthritis or osteo-arthritis. The drug or placebo was administered by intra-articular injection. All patients receiving 120 mg of tenidap free acid or placebo had knee effusions. Improvement in swelling and improvement in maximum degree of relief (by global assessment) over placebo was observed at early times post dose. However, at 2 weeks post dose the improvement was less evident. Also, the determination of plasma levels of tenidap indicated rapid efflux of the drug from the joint between 1–2 hours post dose. These observations are similar to those reported with short-acting corticosteroids. Based on these clinical observations it was concluded that a longer-acting, intra-articular dosage form of tenidap and other oxindoles would be necessary for effective treatment in rheumatoid-arthritis. B. H. Littman, et al. Arthritis and Rheumatism 35/9 Suppl., 8341, 1992.

Sparingly soluble salts of oxindole-1-carboxamides were synthesized and evaluated for development of an intra-articular dosage form. Calcium, magnesium, lidocaine and benzathine salts showed suitable solubility characteristics (see table 3) and benzathine was identified as the most effective salt form on the basis of its low aqueous solubility, slow dissolution rate and superior solid state stability over the other salt forms investigated.

2-Oxindole-1-carboxamides are prepared by procedures described in U.S. Pat. No. 4,556,672, the disclosure of which is hereby incorporated by reference.

Compounds of formula II are prepared by the procedure described in U.S. Pat. No. 5,047,554, the disclosure of which is hereby incorporated by reference.

Calcium, magnesium, ω-diethylamino-2,6-dimethylacetanilide (lidocaine), and N,N-dibenzylethylenediamine (benzathine) salts of 2-oxindole-1-carboxamides are readily prepared by dissolving or suspending the 2-oxindole-1-carboxamide in a suitable liquid such as glycerine, ethanol, isopropanol or dimethylacetamide and adding equivalent amounts of calcium oxide, calcium hydroxide, magnesium oxide, magnesium hydroxide, lidocaine or benzathine either neat or in the same or different liquid at room temperature or warmed to about 50° C. to 100° C. Upon cooling, the salt may precipitate or may be precipitated by addition of a second liquid such as water or aqueous alcohol.

The salts so obtained may be purified by recrystallization from a suitable solvent. In vitro release rates of 2-oxindole-1-carboxamide from the salts are shown in table 3 below.

Preferred salts are tenidap calcium and tenidap benzathine.

In an irritation study in albino rabbits, a single intra-articular dose of 0.5 ml of a tenidap free acid suspension that contained 30 or 60 mg of tenidap (free acid) activity/ml was shown to be non-irritating. In a separate group of rabbits dosed in a similar manner with the more concentrated tenidap suspension, the assay results indicated that in excess of 50% of the single 30 mg dose was cleared from the knee joint at 2 hours post dose and that practically all of the compound was cleared from the joint by 24 hours post dose.

The calcium and the benzathine salts of tenidap were selected to develop a long-acting dosage form. In in vitro studies, these salts were found to have substantially slower dissolution rates when compared with tenidap free acid. Formulations were prepared by suspending the appropriate amount of the calcium salt or benzathine salt form of the compound in the clinical vehicle (Tenidap Suspension Vehicle; See Table 1) to obtain a concentration of 120 mg of the active moiety (tenidap free acid)/ml.

Suspensions of tenidap salts were wet-milled for 12 hours to reduce the particle size to approximately 10μ. The test suspensions were maintained at room temperature until they were used for dosing. The tenidap calcium suspension was bright yellow, opaque, and somewhat viscous, while the tenidap benzathine suspension was pale yellow and opaque. Prior to dosing each animal, the vial containing the appropriate test suspension was agitated vigorously to ensure homogeneity.

Seventeen male, adult New Zealand White (random-bred) rabbits, weighing 3.34 to 4.40 kilograms, were used in the study. On the day prior to dosing, the area around the knee joint on both hind legs of each animal was clipped free of hair using an electric clipper. On the day of dosing, eight of the animals were given a single 0.5 ml intra-articular injection of the tenidap calcium suspension (intended dose equivalent to 60 mg of tenidap free acid) into the left knee. A second group of eight rabbits was given a single 0.5 ml intra-articular injection of the tenidap benzathine suspension (intended dose equivalent to 60 mg of tenidap free acid) into the left knee. The right knee of each animal was not injected. The remaining rabbit served as an undosed control for baseline purposes.

The animals were manually restrained in a supine position during the brief dosing procedure and were not anesthetized. Each injection was made through the patellar ligament into the intra-articular space using a sterile, 1 ml plastic, disposable syringe equipped with a sterile, disposable, ⅝-inch, 25 gauge hypodermic needle. All animals were returned to their respective cages after dosing.

The rabbits were observed intermittently throughout the day of dosing and daily thereafter for clinical signs of discomfort and/or systemic toxicity and for gross changes at the injection site. Each day, the animals' food consumption was evaluated, and individual body weights were recorded. Plasma and both knee joints were obtained from the undosed animal and from two rabbits/treatment group each at 2, 24, 48 and 120 hours after dosing.

At the appropriate time post dose, approximately 5 ml of blood were taken from each animal by cardiac puncture, and the animals were sacrificed by injection of an overdose of sodium pentobarbital into a marginal ear vein. The blood was heparinized, and the plasma was collected. Both knee joints of each rabbit were excised (the joint space was not opened). Plasma and knee joints were stored frozen until assayed. The concentration of tenidap in plasma and the knee joints was determined by high performance liquid chromatography with ultraviolet detection. In this assay, the limit of detection for tenidap was 0.5 μg/ml. The procedures used for the determination of tenidap in the knee joint were as follows.

Following excision of the entire knee joint, the knee was placed in la plastic bag and frozen until use. For drug extraction, the knee was partially thawed (~15 minutes). The tissue was excised from the joint using a scalpel and scissors, and placed into three heavy-walled Nalgene (100 ml) centrifuge tubes. The remaining bone material was separated into three portions, cut into small pieces with a bone cutter, and combined with the tissue portions in the tubes (i.e., each knee was cut into three segments for extraction).

Thirty milliliters of methanol/1% triethylamine (TEA) [solvent] were added to each tube, and the tissue was homogenized to a paste using a Polytron (speed setting 11 for 2 minutes). The tubes were centrifuged (International Centrifuge, setting 50 for 10 minutes), and the supernatant was decanted into a 500 ml round bottom flask. The pellet was washed three times with solvent, and the washes were combined in the round bottom flask.

The solvent was removed under vacuum (Buchi RE 121 Rotavap, at 40°–50° C., at 80 kPa). The residue was reconstituted with a 10 ml portion of the solvent by vigorously vortexing to disperse the film. A 5 ml portion of the above solution was pipetted into a 10 ml volumetric flask and brought to volume with 0.1 M TRIS buffer (24.2 g TRIS, 4.6 ml $H_3PO_4$, 2 L $H_2O$). Tenidap was added to the sample as an internal standard at approximately 2 μg/ml in the sample).

Intact tenidap levels were then quantitated using a high performance liquid chromatography procedure. The chromatographic conditions were as follows: Waters Novapak C-18 column (39 mm×150 mm: 5μ particle size); 55% methanol, 45% 0.025 M TRIS buffer mobile phase (pH 6.3 with $H_3PO_4$); flow rate 1 ml/min; detection at 276 nm).

Tenidap levels in both plasma and knee joint following the intra-articular administration of the calcium and benzathine salts are presented in Table 2. For comparative purposes, the results from an earlier study with a tenidap free acid suspension are also included.

A previous study indicated that a 30 mg dose of the free acid was essentially cleared from the knee joint within 24 hours of injection. However, in the present invention, after intra-articular administration of a 60 mg dose of either the calcium or benzathine salt of tenidap, 12–14% of the dose was still present in the knee joint at 24 hours post dose. In addition, there were detectable levels of tenidap in the knee joint at 48 hours and possibly 5 days post dose. Similarly, tenidap was still detectable in the plasma 5 days after dosing with either salt form.

TABLE 1

Composition of Tenidap Suspension Vehicle

| Ingredient | mg/ml |
| --- | --- |
| Polyethylene Glycol 3350 NF/FCC | 30.00 |
| Polysorbate 80 NF | 3.00 |
| Sodium Chloride USP/FCC | 9.00 |
| Benzyl Alcohol NF | 10.00 |
| Citric Acid USP | 9.60 |
| Sodium Hydroxide NF/FCC | 2.70[a] |
| Water for Injection USP | 935.70 |

[a]Approximate amount used as an 8% (w/w) solution to adjust pH

TABLE 2

Individual Concentrations of Tenidap in the Plasma and Knee Joint of Male Albino Rabbits Following a Single Intra-articular Injection[a]

| Treatment | Rabbit # (05-9) | Hours Post Dose | Plasma Conc. (μg/ml) | Total mg Tenidap in Tissues of Knee Joint | Percent of Injected Tenidap Remaining in Knee Joint |
| --- | --- | --- | --- | --- | --- |
| Undosed Control | 31323 | NA | <0.5[c] | — | — |
|  | 31324 | NA | <0.5 | — | — |
|  | 31297 | NA | <0.5 | — | — |
|  | 31367 | NA | <0.7[d] | — | — |
| Tenidap Free Acid | 31314 | 2 | 13.2 | 9.9 | 33 |
| Suspension (equivalent to | 31315 | 2 | 20.3 | 11.7 | 39 |
| a dose of 30 mg of tenidap | 31316 | 2 | 19.7 | 9.6 | 32 |
| free acid) | 31317 | 24 | 1.3 | 0.10 | 0.3 |
|  | 31318 | 24 | 0.6 | 0.02 | 0.08 |
|  | 31319 | 24 | .07 | <0.01 | 0.02 |
|  | 31320 | 48 | <0.5 | <0.01 | — |
|  | 31321 | 48 | <0.5 | <0.01 | — |
|  | 31322 | 48 | <0.5 | <0.01 | — |
| Tenidap Calcium | 31333 | 2 | 18.0 | 16 | 30.2 |
| Suspension (equivalent to | 31368 | 2 | 18.0 | 13 | 24.5 |
| a dose of 60 mg of tenidap | 31369 | 24 | 9.2 | 7.6 | 14.3 |
| free acid) | 31370 | 24 | 29.0 | 7.7 | 14.5 |
|  | 31371 | 48 | 7.7 | 5.2 | 9.8 |

TABLE 2-continued

Individual Concentrations of Tenidap in the Plasma and Knee Joint of Male Albino Rabbits Following a Single Intra-articular Injection[a]

| Treatment | Rabbit # (05-9) | Hours Post Dose | Plasma Conc. (μg/ml) | Total mg Tenidap in Tissues of Knee Joint | Percent of Injected Tenidap Remaining in Knee Joint |
|---|---|---|---|---|---|
| | 31372 | 48 | 7.4 | 4.2 | 7.9 |
| | 31335 | 120 | 1.6[e] | 6.9[e] | 13.0[e] |
| | 31334 | 120 | 0.7 | <0.01 | — |
| Tenidap Benzathine | 31379 | 2 | 7.0 | 16 | 31.4 |
| Suspension (equivalent to | 31380 | 2 | 7.5 | 15 | 29.4 |
| a dose of 60 mg of tenidap | 31381 | 24 | 18.0 | 7.6 | 14.9 |
| free acid) | 31382 | 24 | 15.0 | 6.3 | 12.4 |
| | 31383 | 48 | 3.4 | 0.70 | 1.4 |
| | 31384 | 48 | 9.0 | 1.1 | 2.2 |
| | 31338 | 120 | 0.7 | <0.5 | — |
| | 31386 | 120 | 1.9[e] | 3.2[e] | 6.3[e] |

[a]Animals were given a single 0.5 ml intra-articular injection of the appropriate suspension of tenidap into the left knee. The free acid was administered as a 60 mg/ml suspension, while the tenidap calcium and benzathine suspensions contained 120 mg/ml.
[b]Values for tenidap calcium and tenidap benzathine suspensions are based on doses of 53 and 51 mg of tenidap, respectively, as per the results of the assay of the test suspensions.
[c]The assay limit of detection was 0.5 μg/ml.
[d]An unexplained peak with the same retention time as tenidap as determined by the HPLC assay.
[e]What appeared to be test suspension was evident in the muscles below the knee joint.

TABLE 3

In Vitro Release Rates of Tenidap from Suspensions

| Formulation | Percent of drug released after 24 hours |
|---|---|
| Free Acid Suspension (5μ particles) | 60 |
| Free acid Suspension (10μ particles) | 52 |
| Tenidap Calcium Suspension | 17 |
| Tenidap Magnesium Suspension | 30 |
| Tenidap Lidocaine Suspension | 34 |
| Tenidap Benzathine Suspension (Low Viscosity) | 5 |
| Tenidap Benzathine Suspension (High Viscosity) | 2 |
| Tenidap Benethamine Suspension | 19 |

EXAMPLE 1

Benzathine Salt of Tenidap

A 16.05 gram (50 millimole) portion of tenidap was stirred in 300 milliliters of isopropyl alcohol. The resulting yellow slurry was heated to 50° C. At 50° C. a solution of 6.6 grams (27.5 millimoles) of benzathine in 60 milliliters of isopropyl alcohol was added all at once. The yellow slurry rapidly turned light orange. After about one minute the orange slurry began to turn pale yellow and thicken slightly. The heat was removed and the reaction was stirred under ambient conditions for 2 hours. The product was collected by filtration and washed with a 50 milliliter portion of isopropyl alcohol. The pale yellow solids were dried at 45° C. in vacuo. The yield was 99% as the crystalline bis salt. The product purity was 72% activity which is correct for the bis salt. The product can be recrystallized by dissolution in warm N,N-dimethylacetamide and reprecipitation by the addition of 4 or more volumes of isopropyl alcohol.

EXAMPLE 2

Tenidap Calcium Salt Dihydrate

A 64.15 gram (200 mmol) portion of tenidap was combined with 7.94 grams (105 mmol) of 98% calcium hydroxide in 160 milliliters of dimethylacetamide. The resulting thick slurry was heated to 65° C. for 15 minutes yielding a hazy solution. The reaction was cooled to 25° C. and filtered to sparkle the solution. Precipitation was accomplished by the addition of 480 milliliters of a 50/50 mixture of isopropanol and water. The thick slurry was granulated at ambient temperature for one hour. The partially crystalline product was collected by filtration. This product was charged to 1240 milliliters of a 9/1 mixture of isopropanol and water. The slurry was heated to reflux for one hour. During this reflux period the slurry changed in color from yellow to a deep orange as the dihydrate was formed. The slurry was cooled to 60° C. and filtered at that temperature. The collected crystalline product was dried in vacuo at 45° C. A yield of 83% was obtained using this procedure.

The product is the bis salt (5.6% calcium) and the dihydrate (5.03% water). Micro analysis was correct for this product and crystallinity was confirmed by both microscopy and X-ray powder diffraction.

I claim:

1. A salt selected from the group consisting of benzathine and lidocaine salts of a compound of the formula:

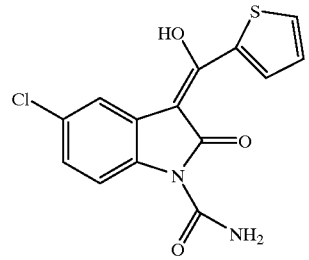

5-chloro-2,3-dihydro-3-(hydroxy-2-thienylmethylene)-2-oxo-1-H-indole-1-carboxamide;

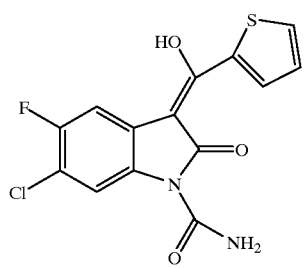

5-fluoro-6-chloro-2,3-dihydro-3-(hydroxy-2-thienylmethylene)-2-oxo-1-H-indole-1-carboxamide.

2. A benzathine salt of a compound of the formula:

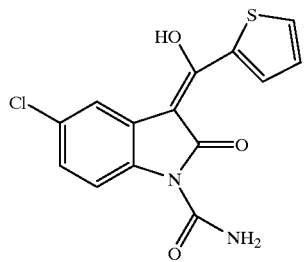

5-chloro-2,3-dihydro-3-(hydroxy-2-thienylmethylene)-2-oxo-1-H-indole-1-carboxamide.

3. A method of treating pain and inflammation of joint disease comprising administering by way of intra-articular injection a therapeutically effective amount of a salt according to claim 1 into an inflamed joint of a mammal in need of such treatment.

4. A pharmaceutical composition for administration by way of intra-articular injection comprising a salt according to claim 1 and a pharmaceutically acceptable carrier therefor.

5. A method of treating pain and inflammation of joint disease comprising administering by way of intra-articular injection a therapeutically effective amount of a salt according to claim 2 into an inflamed joint of a mammal in need of such treatment.

6. A pharmaceutical composition for administration by way of intra-articular injection comprising a salt according to claim 2 and a pharmaceutically acceptable carrier therefor.

* * * * *